(12) United States Patent
Barth

(10) Patent No.: US 8,459,452 B1
(45) Date of Patent: Jun. 11, 2013

(54) DISPOSABLE TATTOO INK CONTAINER

(75) Inventor: Mario Barth, Washington Township, NJ (US)

(73) Assignee: Intenze Products, Inc., Rochelle Park, NJ (US)

( * ) Notice: Subject to any disclaimer, the term of this patent is extended or adjusted under 35 U.S.C. 154(b) by 0 days.

(21) Appl. No.: 13/588,354

(22) Filed: Aug. 17, 2012

(51) Int. Cl.
*B65D 85/00* (2006.01)

(52) U.S. Cl.
USPC .......................... 206/224; 206/1.7

(58) Field of Classification Search
USPC ........... 215/372, 373, 374, 375, 376; 206/1.7, 206/371, 81, 524.1, 575, 224
See application file for complete search history.

(56) References Cited

U.S. PATENT DOCUMENTS

| | | | | |
|---|---|---|---|---|
| 2,264,489 A * | 12/1941 | Tiegler et al. | ................. | 248/694 |
| 2,908,473 A * | 10/1959 | Snyder | ......................... | 248/683 |
| 3,229,949 A * | 1/1966 | Chaconas | ................ | 248/346.11 |
| 3,542,261 A * | 11/1970 | Greenberg | ..................... | 222/576 |
| 4,040,549 A * | 8/1977 | Sadler | ........................... | 224/483 |
| 4,771,902 A * | 9/1988 | Teng | .............................. | 215/376 |
| 4,936,449 A * | 6/1990 | Conard et al. | ................ | 206/366 |
| 5,678,684 A * | 10/1997 | Wright | ........................ | 206/204 |
| 5,833,649 A * | 11/1998 | Atef | ............................. | 604/500 |
| 2012/0221036 A1* | 8/2012 | Ahmann et al. | .............. | 606/186 |

* cited by examiner

*Primary Examiner* — Jacob K Ackun
(74) *Attorney, Agent, or Firm* — Epstein Drangel LLP; Robert L. Epstein

(57) ABSTRACT

A single use, disposable container for tattoo ink has a generally cylindrical body defining a reservoir for retaining tattoo ink, a base and a cap. The base has a bottom surface. At least one member extends radially from the bottom surface of the base. A layer of adhesive is provided on the bottom surface of the base, but not on the under surface of the radially extending member. A removable protective layer is situated over the adhesive layer. The protective layer has a radially extending portion aligned with the member radially extending from the base. The radially extending base member increases the stability of the container, facilitates removal of the cap from the container body and provides for easy removal of the protective sticker from the adhesive layer.

5 Claims, 3 Drawing Sheets

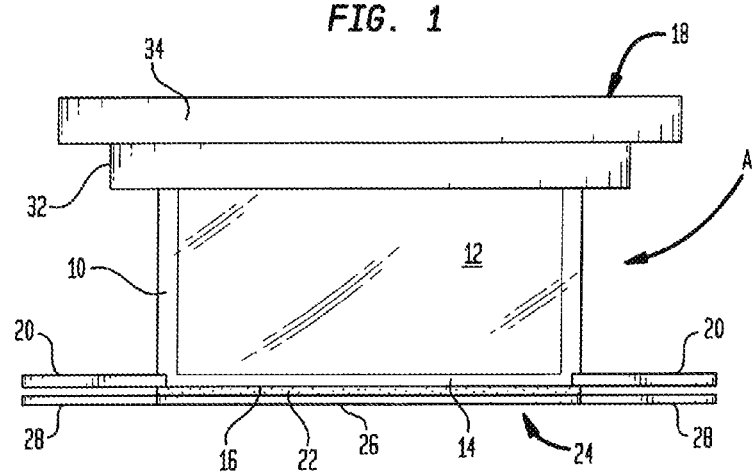
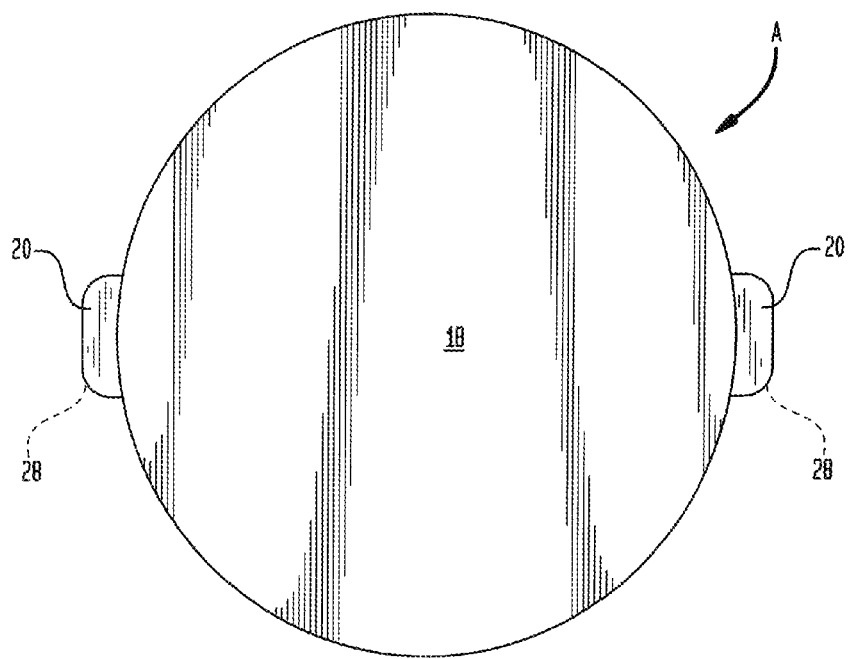

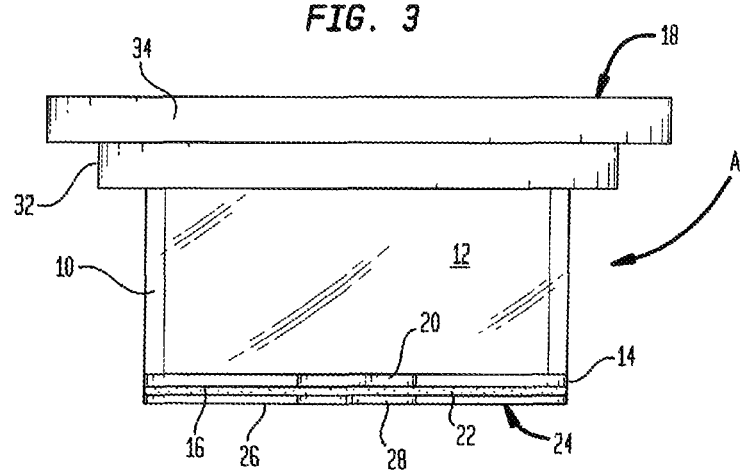
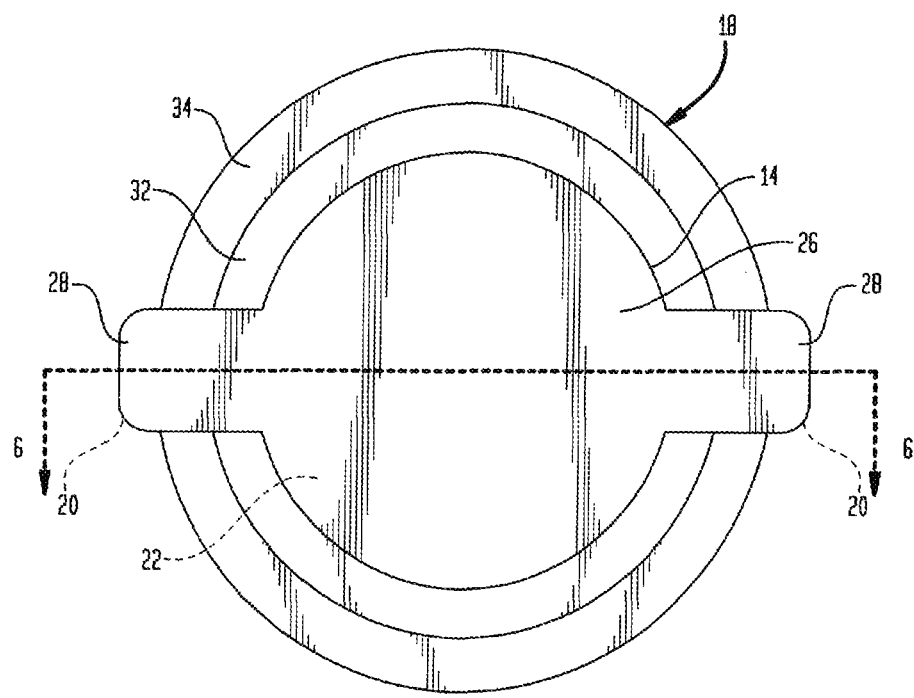

DISPOSABLE TATTOO INK CONTAINER

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The present invention relates to tattoo ink and more particularly to a disposable container for tattoo ink which is safer for the client because it is intended for a single use, and is advantageous for the tattoo artist because it is convenient to transport and easy to use in the tattoo booth.

2. Description of Prior Art Including Information Disclosed Under 37 CFR 1.97 and 1.98

It is well known that the use of ink from the same container for multiple tattoo clients can result in the transfer of disease, even if the instruments used are properly sterilized. However, small amounts of ink of various colors may be required for a particular client and discarding containers partially filled with ink after each client is wasteful and expensive. As a result, a unique and inexpensive disposable ink container intended for single use only has been developed to eliminate the possibility of cross-contamination and at the same time reduce the costs involved in having fresh ink available for each client.

The single use container of the present invention has been designed to be travel safe and durable. It includes structure which increases the stability container. It also includes an adhesive layer on the bottom of the container which allows the container to adhere to a surface in the tattoo booth such that the container cannot be accidently knocked over or moved out of position as the tattoo artist is working, while at the same time allowing the tattoo artist to have both hands free to create the tattoo.

A removable sticker is provided to seal and protect the adhesive layer during transport and handling of the container. The container includes structure provided to facilitate removal of the protective sticker.

The container is provided with a plastic cap which fits snuggly on the container body to prevent the tattoo ink from being spilled or contaminated by the environment during transport and handling. The container is provided with structure which facilitates removal of the cap.

The structure which increases the stability of the container, facilitates removal of the cap, and allows easy removal of the protective sticker is the same structure. As a result, the design of the single use container of the present invention is simple, allowing the container to be fabricated inexpensively such that it is economical enough for single use and yet has the safety, transportability and ease of use sought by tattoo artists not available from conventional tattoo ink containers.

BRIEF SUMMARY OF THE INVENTION

The present invention relates to a disposable container for tattoo ink which includes a generally cylindrical body defining a reservoir for retaining ink, a base and a cap. The base has a bottom surface. At least one member radially extends from the bottom surface to increase the stability of the container. A layer of adhesive is provided on the bottom surface of the container such that the position of the container on a surface in the tattoo booth can be fixed while the tattoo artist is working.

The container has a removable protective sticker situated over the adhesive layer to seal and protect the adhesive layer during transport and handling. The protective sticker has a radially extending portion. The radially extending portion is preferably aligned with the radially extending member of the container.

The extending container member has a bottom surface. The adhesive layer substantially covers bottom surface of the container but does not cover the bottom surface of the extending member of the container. That allows the extending portion of the sticker to be readily separated from the extending member of the container to facilitate removal of the sticker.

The extending member of the container preferably takes the form of a tab. More preferably, the extending container member takes the form of first and second tabs. Most preferably, the first and second tabs extend from the container base in substantially opposite radial directions.

The radially extending portion of the sticker is substantially aligned with the member radially extending from the container base. Preferably, the protective sticker includes first and second radially extending portions which substantially align with the first and second tabs, respectively.

The container body is formed of light transmissive material such that the color and remaining quantity of the tattoo ink in the container can be readily observed.

The container body comprises a rim. The cap includes a wall defining a recess into which the container rim is adapted to be received. The cap also includes a cover fixed to the cap wall. Preferably, the cover extends beyond the cap wall.

In accordance with another aspect of the present invention, a single use container for tattoo ink is provided including a body defining an ink reservoir, a base and a cap. The base includes means for adhering the container to a surface. A removable sticker is provided to seal and protect the adhesive means. Means extending from the base are provided for facilitating the removal of the protective sticker.

The cap is removable from the container body. Means are provided for facilitating the removable of the cap.

Preferably, the means for facilitating removal of the protective sticker and the means for facilitating removal of the cap are the same means.

That means includes a member radially extending from the base of the container.

The container also includes means for increasing the stability of the container.

The means for facilitating removal of the protective layer, the means for facilitating removal of the cap and the means for increasing the stability of the container are preferably the same means. That means includes at least one member radially extending from the base.

BRIEF DESCRIPTION OF THE SEVERAL VIEWS OF DRAWINGS

To these and to such other objects that may hereinafter appears, the present invention relates to a disposable container for tattoo ink as described in detail in the following specification and recited in the annexed claims, taken together with the accompanying drawings, in which like numerals refer to like parts and in which:

FIG. 1 is a front elevation view of the container of the present invention;

FIG. 2 is a top elevation view of the container;

FIG. 3 is a side elevation view of the container;

FIG. 4 is a bottom elevation view showing the protective stick in place;

DETAILED DESCRIPTION OF THE INVENTION

Figure 5:
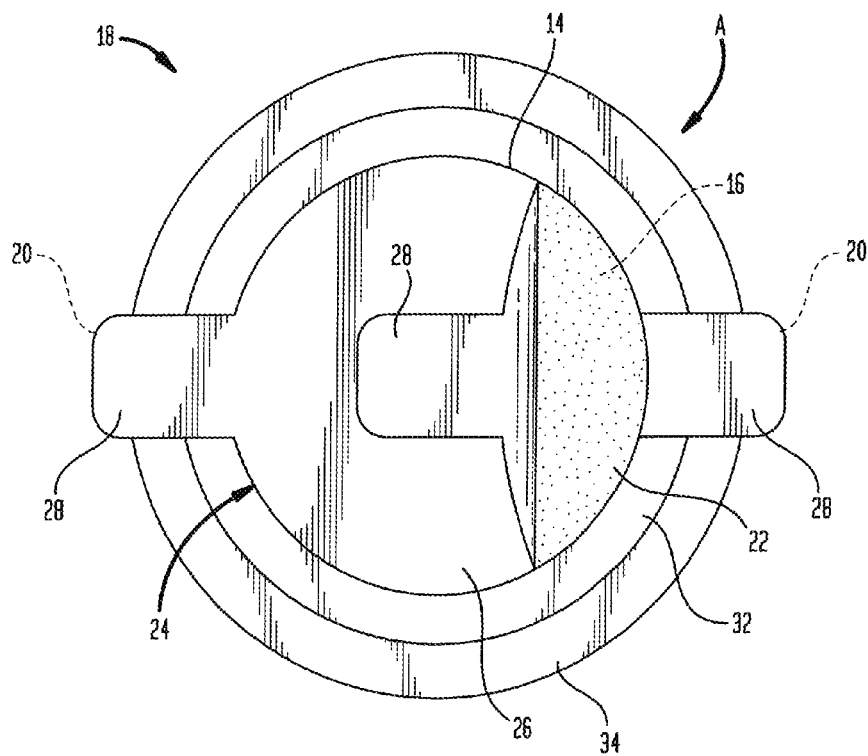
FIG. 5 is a bottom elevation view of the container with a portion of the protective sticker pealed back.
Figure 6:
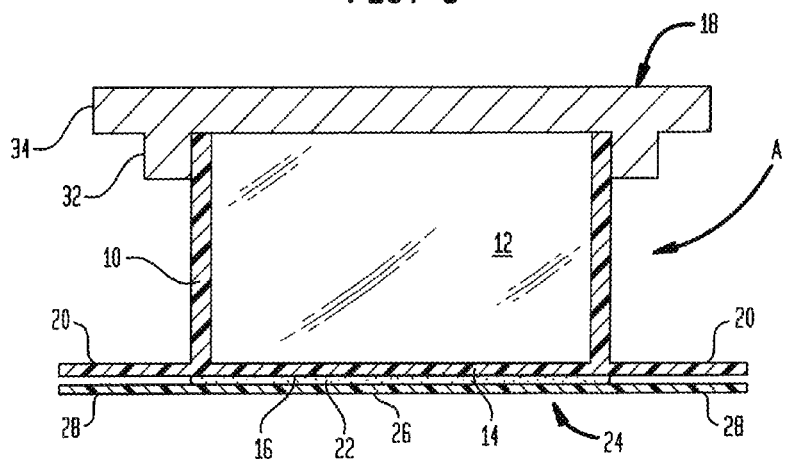
FIG. 6 is a cross-sectional view of the container take along the line 6-6 of FIG. 4.

As seen in the Figures, the present invention relates to disposable container for tattoo ink, generally designated A, designed for a single use, that is, use in creating a tattoo on one client. Container A includes a generally cylindrical body formed of wall 10 defining a reservoir 12 for retaining tattoo ink Wall 10 is preferably made of light transmissive plastic such that the color of the ink and the quantity of the ink in reservoir 12 can be readily observed.

Container A has a base 14. A removable cap 16 is provided to cover the ink reservoir 12 of the container.

Base 14 has a round bottom surface 18. Radially extending from bottom surface 18 are one or more members 20. Preferably, members 20 are integral with the base. Preferably, members 20 take the form of tabs with rounded outer corners. Preferably, tabs 20 extend from base 14 in opposite directions. While only two members 20 are illustrated, the number of radially extending members can vary as needed.

A layer of adhesive 22 is applied to the bottom surface 16 of base 14. Adhesive layer 22 is covered by a removable protective sticker or film 24 having a round central portion 26. Protective sticker 24 has portions 28 radially extending from central portion 26 which align with tabs 20 extending from base 14. Preferably, portions 28 are integral with central portion 26 of the sticker. Preferably, portions 28 are substantially the same size and shape as tabs 20.

Adhesive layer 22 substantially covers the bottom surface 16 of base 14 of the container body but not bottom surfaces of members 20. Thus, the top surfaces of portions 28 of the protective layer do not stick to the bottom surfaces of members 20 and portions 28 can be easily separated from members 20 such that sticker 24 can be readily peeled back off the adhesive layer, as illustrated in FIG. 5.

Wall 10 of the container has an upper portion or rim 30. Cap 18 includes a generally cylindrical wall 32 and a cover member 34. Wall 32 and cover member 34 of cap 18 define a recess into which rim 30 of wall 10 is received. Preferably, the cap fits snuggly over wall 10. As seen in the figures, cover member 34 extends beyond wall 32 and forms an overhanging edge which can be readily grasped by the tattoo artist to remove the cap from the body of the container.

In use, the tattoo artist selects a container with the desired color ink for creating the tattoo on a client. The artist grasps one of the portions 28 of the protective sticker and peels the sticker back so as to expose the adhesive layer on the bottom surface of the base of the container. Portions 28 of the sticker are easy to grasp because there is no adhesive between portions 28 of the sticker and members 20 of the base.

After the sticker is completely removed, the container with the exposed adhesive layer on the bottom surface is placed on a horizontal surface such as a table in proximity to the tattoo artist so it can be easily reached. The adhesive prevents the container from being accidentally knocked over or moved away from the desired position.

The radially extending members 20 of the container provide extra stability for the container. They also facilitate removal of the cap by providing a convenient place for the artist to hold with one hand while the artist grabs the cover member of the cap with the other hand and pries the cap off the base of the container to expose the ink reservoir. The tattoo artist is now ready to proceed to create the tattoo. Once the tattoo is completed, the container is removed from the surface to which it adhered and is discarded.

It will now be appreciated that the present invention relates to a single use disposable container for tattoo ink with includes a body defining an ink reservoir, a base and a cap. The base has means for adhering the container to a surface. A removable protective sticker for the adhering means is provided. Means extending the body are provided for facilitating the removal of the protective layer.

The cap is removable from the container body. Means are provided for facilitating the removal of the cap.

Further, means are provided for increasing the stability of the container.

The means for facilitating removal of the protective layer, the means for facilitating removal the cap and the means for increasing the stability of the container preferably all are the same means. Those means include at least one member radially extending from the base. Preferably, more than one such member is provided, preferably in pairs of oppositely extending members. In the preferred embodiment, the members take the form of tabs.

While only a single preferred embodiment of the present invention has been disclosed for purposes of illustration, it is obvious that many modifications and variations could be made thereto. It is intended to cover all of those modifications and variations which fall within the scope of the present invention, as defined by the following claims.

I claim:

1. A disposable container for tattoo ink comprising a body formed of a substantially cylindrical side wall and a circular base integral with said side wall, said side wall and said base defining a reservoir for retaining ink, first and second tabs extending in substantially opposite directions from said base, in the plane of said base, said base having a bottom exterior surface, each of said tabs have an exterior bottom surface, said bottom surface of said base and said bottom surfaces of said tabs forming the exterior bottom surface of said body, a layer of adhesive situated on said exterior bottom surface of said body, except on said bottom surfaces of said tabs and a removable protective layer situated over said adhesive layer, said protective layer comprising a circular central portion aligned with said base, and first and second portions extending outwardly from said central portion of said protective layer and aligned with said first and second tabs, respectively.

2. The container of claim 1 wherein said body is formed of light transmissive material.

3. The container of claim 1 wherein said body comprises a rim and wherein said cap comprises a wall defining a recess into which said rim is adapted to be received.

4. The container of claim 3 wherein said cap comprises a wall defining a recess into which said rim is adapted to be received and a cover fixed to said wall.

5. The container of claim 4 wherein said cover extends beyond said wall.

\* \* \* \* \*